United States Patent
Wheeler

(10) Patent No.: US 9,366,605 B2
(45) Date of Patent: Jun. 14, 2016

(54) HISTOLOGICAL SPECIMEN TREATMENT APPARATUS AND METHOD

(76) Inventor: Steven Paul Wheeler, Rancho Palos Verdes, CA (US)

(*) Notice: Subject to any disclaimer, the term of this patent is extended or adjusted under 35 U.S.C. 154(b) by 0 days.

(21) Appl. No.: 13/396,541

(22) Filed: Feb. 14, 2012

(65) Prior Publication Data
US 2012/0202241 A1      Aug. 9, 2012

Related U.S. Application Data

(63) Continuation of application No. 12/128,523, filed on May 28, 2008, now abandoned.

(51) Int. Cl.
| G01N 1/00 | (2006.01) |
| G01N 1/30 | (2006.01) |
| G01N 1/31 | (2006.01) |
| G01N 1/36 | (2006.01) |

(52) U.S. Cl.
CPC ... *G01N 1/31* (2013.01); *G01N 1/36* (2013.01)

(58) Field of Classification Search
USPC .......................................................... 219/678
See application file for complete search history.

(56) References Cited

U.S. PATENT DOCUMENTS

| 2,150,757 A |   | 3/1939  | Bodine   |         |
| 2,684,925 A |   | 7/1954  | Ferrari  |         |
| 3,389,052 A |   | 6/1968  | Theodore |         |
| 3,456,300 A | * | 7/1969  | Pickett  | 425/117 |
| 3,546,334 A |   | 12/1970 | Lerner   |         |
| 3,674,040 A |   | 7/1972  | Howells  |         |
| 3,892,197 A |   | 7/1975  | Kinney et al. |    |
| 3,961,097 A |   | 6/1976  | Gravlee  |         |
| 3,995,022 A |   | 11/1976 | Heanley  |         |
| 4,099,483 A |   | 7/1978  | Henderson |        |

(Continued)

FOREIGN PATENT DOCUMENTS

| DE | 4400815 A1 | 7/1995 |
| EP | 822403 B1  | 7/1998 |

(Continued)

OTHER PUBLICATIONS

Dimethyl sulfoxide (Retrieved on Sep. 24, 2012 from the Internet: <URL: http://www.sigmaaldrich.com/chemistry/solvents/dimethyl-sulfoxide-center/physical-properties.html>).*

(Continued)

*Primary Examiner* — Robert T Crow
*Assistant Examiner* — Joseph G Dauner
(74) *Attorney, Agent, or Firm* — Fish & Richardson P.C.

(57) ABSTRACT

Method and apparatus for processing tissue specimens against decomposition, putrefaction and autolysis which use a simple three step procedure in a single vessel or container. First, the specimens are saturated with a solvent mixture of a ketone and a hydrocarbon, e.g., an Acetone/Hexane or an Acetone/Xylene mixture, to dissolve lipids and other cellular solutes. The container is then flooded with melted Paraffin. In a last step, the solvent mixture is vaporized and evacuated from the container, allowing the melted Paraffin to replace the vaporized solvent and impregnate the specimens. Raw, i.e., non-processed and non-burred specimens up to 5 mm thick can be processed in about 60 minutes. A solvent regenerator distills the evacuated solvent; and converts vent waste gases into carbon dioxide and water through a thermocatalytic oxidizer.

21 Claims, 3 Drawing Sheets

(56) References Cited

U.S. PATENT DOCUMENTS

| | | | |
|---|---|---|---|
| 4,141,312 A | 2/1979 | Louder | |
| 4,199,558 A | 4/1980 | Henderson | |
| 4,221,823 A | 9/1980 | Pearson | |
| 4,300,243 A | 11/1981 | Baumgartner | |
| 4,545,831 A | 10/1985 | Ornstein | |
| 4,569,647 A * | 2/1986 | McCormick | 425/117 |
| 4,656,047 A | 4/1987 | Kok et al. | |
| 4,670,386 A | 6/1987 | Sugaar | |
| 4,681,996 A | 7/1987 | Collins | |
| 4,784,873 A | 11/1988 | Kienecker et al. | |
| 4,835,354 A | 5/1989 | Collins | |
| 4,839,194 A | 6/1989 | Malluche | |
| 4,882,128 A | 11/1989 | Hukvari | |
| 4,891,239 A | 1/1990 | Dudley | |
| 4,911,915 A | 3/1990 | Fredenburgh | |
| 4,992,763 A | 2/1991 | Bert | |
| 4,994,237 A | 2/1991 | Login | |
| 5,023,187 A | 6/1991 | Koebler | |
| 5,030,929 A | 7/1991 | Moeller | |
| 5,049,510 A | 9/1991 | Repasi | |
| 5,068,086 A | 11/1991 | Sklenak | |
| 5,089,288 A * | 2/1992 | Berger | A01N 1/00 |
| 5,104,640 A | 4/1992 | Stokes | |
| 5,122,633 A | 6/1992 | Moshammer | |
| 5,230,865 A | 7/1993 | Hargett | |
| 5,244,787 A | 9/1993 | Key | |
| 5,256,571 A | 10/1993 | Hurley | |
| 5,289,140 A | 2/1994 | Jorgenson | |
| 5,318,795 A | 6/1994 | Stokes | |
| 5,387,397 A | 2/1995 | Strauss | |
| 5,401,625 A | 3/1995 | Robinson | |
| 5,431,952 A | 7/1995 | Ocello | |
| 5,432,056 A | 7/1995 | Hartman | |
| 5,460,797 A | 10/1995 | Ryan | |
| 5,532,462 A | 7/1996 | Butwell | |
| 5,609,820 A * | 3/1997 | Bridges et al. | 422/23 |
| 5,625,706 A | 4/1997 | Lee | |
| 5,672,696 A | 9/1997 | Wang | |
| 5,679,333 A | 10/1997 | Dunphy | |
| 5,712,605 A | 1/1998 | Flory | |
| 5,758,033 A | 5/1998 | Bernstein | |
| 5,782,897 A | 7/1998 | Carr | |
| 5,796,080 A | 8/1998 | Jennings | |
| 5,830,417 A | 11/1998 | Kingston | |
| 5,849,517 A | 12/1998 | Ryan | |
| 5,875,286 A | 2/1999 | Bernstein | |
| 6,011,247 A | 1/2000 | Grillo | |
| 6,042,874 A | 3/2000 | Visinoni | |
| 6,072,086 A | 6/2000 | James | |
| 6,183,995 B1 | 2/2001 | Burmer | |
| 6,204,375 B1 | 3/2001 | Lader | |
| 6,207,408 B1 | 3/2001 | Essenfeld | |
| 6,248,535 B1 | 6/2001 | Danenberg | |
| 6,258,329 B1 | 7/2001 | Mutterer | |
| 6,268,596 B1 | 7/2001 | Lauf | |
| 6,291,180 B1 | 9/2001 | Chu | |
| 6,404,906 B2 | 6/2002 | Bacus | |
| 6,586,713 B2 | 7/2003 | Essenfeld | |
| 6,615,763 B2 | 9/2003 | Edwards | |
| 6,674,884 B2 | 1/2004 | Bacus | |
| 6,681,035 B1 | 1/2004 | Bamford | |
| 6,793,890 B2 | 9/2004 | Morales | |
| 6,797,928 B2 | 9/2004 | Giberson | |
| 6,892,197 B2 | 5/2005 | Eda | |
| 6,930,292 B1 | 8/2005 | Winther | |
| 6,951,663 B1 | 10/2005 | Edwards | |
| 7,075,045 B2 | 7/2006 | Visinoni | |
| 2001/0051365 A1 | 12/2001 | Morales | |
| 2002/0177183 A1 | 11/2002 | Giberson | |
| 2005/0090017 A1 * | 4/2005 | Morales | 436/174 |
| 2009/0298172 A1 | 12/2009 | Wheeler | |
| 2012/0202241 A1 | 8/2012 | Wheeler | |

FOREIGN PATENT DOCUMENTS

| | | | |
|---|---|---|---|
| EP | 562877 B1 | 6/2000 | |
| EP | 680243 B1 | 1/2004 | |
| WO | WO8606479 A1 | 11/1986 | |
| WO | WO 9805938 A1 * | 2/1998 | |
| WO | WO9805938 A1 | 2/1998 | |
| WO | WO9909390 A1 | 2/1999 | |

OTHER PUBLICATIONS 2-propanol (Retrieved on Sep. 24, 2012 from the Internet: <URL: http://www.sigmaaldrich.com/chemistry/solvents/2propanol-center. html>).*

Acetic Acid (Retrieved on Sep. 24, 2012 from the Internet: <URL: http://www.safcglobal.com/catalog/product/sial/a6283?null>).*

Polyethylene glycol (Retrieved on Sep. 24, 2012 from the Internet: <URL: http://www.sigmaaldrich.com/etc/medialib/docs/Aldrich/ Product_Information_Sheet/p3265pis.Par.0001.File.tmp/ p3265pis.pdf>).*

Hexane (Retrieved on Sep. 25, 2012 from the Internet: <URL: http://www.sigmaaldrich.com/chemistry/solvents/hexane-center.html>).*

Mujiburohman et al. Separation and Purification Technology. 2006. 48: 85-92.*

PubChem. Retrieved on Aug. 31, 2015 from the internet: http://pubchem.ncbi.nlm.nih.gov/compound/isopropanol#section=Top.*

Liu et al., J. of Supercritical Fluids, 2006, 39:89-101.

Non-final office action dated Aug. 17, 2011 from U.S. Appl. No. 12/128,523, 25 pages.

J. Gmeling et al., Azeotropic Data for Binary Mixtures, 94th Edition of the CRC Handbook of Chemistry and Physics, Taylor & Francis group 2013, pp. 6-210 to 6-228, published 2013.

* cited by examiner

HISTOLOGICAL SPECIMEN TREATMENT APPARATUS AND METHOD

PRIOR APPLICATION

This is a continuation of U.S. patent application Ser. No. 12/128,523, filed 2008 May 28, incorporated herein by reference.

FIELD OF THE INVENTION

The present invention relates to techniques and instrumentation for the preservation of tissue specimens. More specifically, the invention teaches the rapid formation of a matrix by the aggregation of a Paraffin medium that impregnates and protects the original tissue structure and prevents decomposition, putrefaction, and autolysis.

BACKGROUND

Many of the prior art methods of preparing tissue specimens for histology use incubation in separate solutions of phosphate-buffered 10% formalin for fixation, a series of increasing concentrations of ethanol, and/or isopropanol for dehydration, and xylene for clearing tissue of dehydration agent, prior to impregnation. Because of the time required for this process, usually 8 hours or longer, it is customary to complete these separate steps—fixation, dehydration, clearing, and impregnation—overnight in automated mechanical instruments designed for those tasks.

The most rapid tissue preservation methods of the prior art rely on microwave processing which does not maintain the non-aqueous character of the reagents that is required in order to prevent burning of the tissue specimens. Moreover, prior fixation processes are plagued by irreversible damage (e.g., hydrolysis of a phosphodiester bond and/or deamidation) to the structure of nucleic acids (e.g., DNA, and especially RNA) that limits the application of genetic techniques for diagnosis and research. Consequently, most DNA and certainly RNA analysis require special precautions with the handling of material, such as immediate freezing of fresh tissues to prevent degradation that can impair retrospective genetic analysis.

Most microwave reagents have poor diffusivity and will not penetrate the specimen properly without pretreatment. Specimens must be sectioned to about 1.5 mm or less, and most preferably to about 1 mm or less, for the process to work. Specimens also require treatment for 30 minutes or more in a pre-processing solution to harden the specimen, so that it can be sectioned to the required thickness.

In some prior processing devices, when the reagents are evacuated after reacting with the specimens, scale, slime and deposits are formed. Scale forms where it can be tolerated least-on heat transfer surfaces. It is in this location that the conditions necessary to cause the precipitation of salts are found. At areas of heat transfer and low flow rates, there is a significant increase in the dissolved solids concentration. There is also a localized temperature rise. The crystallization of scale on these surfaces is a slow process. This promotes the formation of a fairly well defined crystal growth, especially considering the varying composition present in the used fixative. Slow, in-place crystal growth forms a hard, dense, glassy and highly insulating material that is deposited on the evacuation valves and associated conduit surfaces. Some forms of scale are so tenacious that they resist any type of removal, mechanical or chemical. Scales forming on the moving parts of valves stick together and require replacement of the valves and valve motors.

There are also problems associated with impeded work flow in the pathology laboratory necessitated by the requisite batch processing of specimens, the safety concerns that attend having instruments operating overnight, the risk of possible instrument failures, the need to monitor the instruments, and the waste of using large volumes of reagents for such processing when automated.

Expensive measures are required to prevent exposure of laboratory personnel to noxious fumes and toxic substances associated with the reagents used in this process. Also, the large volumes of reagent waste and Paraffin debris produced by the conventional methodology will pollute the environment if not properly disposed.

Prior art processing of tissue is accomplished in a plurality of reactors requiring manual or robotic handling and transfer of the specimens.

Most significantly, the prior art fails to teach an efficient solvent to remove cellular solutes in a single step.

A typical tissue cell contains: 19.44% ether-extractable material (lipids), 55.13% moisture 18.62% protein, and 5.43% ash. The objective is to remove the lipids and free water and replace them with a preserving compound such as Paraffin. Fixation is the first step in preparing cell and tissue specimens for use in a wide range of clinical and analytical testing. A good fixative should harden cell and tissue components. The chemical process of tissue modification by a fixative is gradual and complex, involving penetration into the tissue and a variety of chemical reactions. Formaldehyde fixatives (formalin) are very reactive electrophilic reagents that fix tissue by covalent bonding to reactive functional groups present in tissue. Neutral Buffered Formalin (NBF) is the most widely used fixative for preserving cell and tissue specimens. It is relatively inexpensive, simple to use, and provides consistent results. NBF developed by the US Armed Forces Institute of Pathology is the exclusive aqueous fixative used in automated tissue processors. The formulation is a 1:10 v/v dilution of 37% w/v formaldehyde in a phosphate buffer.

However, when tissue specimens are processed at an elevated temperature (35-50 degrees C.) for a long period of time, e.g., 2 to 12 hours, solid materials tend to accumulate in the processor. Frequent maintenance is required to prevent instrument failure. Several processing device components can be affected by NBF. They include reservoir connections, rotary valve, retort sensors, overflow sensors, solenoid valves, pressure/vacuum regulator manifolds, process pumps and associated plumbing.

REVIEW OF THE PRIOR ART

US Patent Application Publication No. 20050090017 describes a process for simplified tissue processing; the reagent must be water free to work and not burn the tissue specimens. The mixture contains 25% to 60% per volume acetone, 30% to 55% per volume 2-propanol, and 20% per volume mineral oil. Glacial acetic acid is added at 0.5% per volume and 1% per volume Dimethyl Sulfoxide (DMSO), (non-aqueous admixture). An example is for tissue 1.0 to 2.0 mm, preferably about 1.5 mm. The application omits the required preprocessing of the specimen. The process used aeration to agitate the mixture. Total processing time is 120 minutes. In the disclosure, the applicant fails to normalize the relative concentrations of the non-aqueous blend. The mixture is expressed in volume percent that usually varies with temperature. There is no correction provided for the non-linear blending. When, as expected, Acetic acid catalyzes the esterification (Acid-catalyzed nucleophilic addition) of 2-Propanol yielding an ester and water as equilibrium products, the admixture, once blended, is no longer non-aqueous. An Hydronium ion is present, and condenses Acetone to Diacetone alcohol. The condensation is enhanced by the heater microwaves. Moreover, aeration increases the water concentration.

Recent U.S. Pat. Nos. 6,207,408; 6,586,713; and 6,793,890 addressed to a similar process also fail to deal with condensation products.

U.S. Pat. Nos. 3,892,197; 4,141,312; and 5,049,510 exemplify the conventional method of fixing tissues by incubation in separate solutions of phosphate buffered 10% Formaldehyde, dehydration by increasing concentrations of Ethanol and/Isopropanol, and clearing the tissues of dehydration agents prior to impregnation with Xylene. Because of the time required to perform the several steps, typically eight hours, automated devices are run overnight.

Currently, the most advanced automatic tissue processor of this type is marketed under the brand name TISSUE-TEK by Sakura Finetek of Torrance, Calif. The SAKURA TISSUE-TEK vacuum infiltration processor requires more than eight hours for completion of processing. Baskets holding the cassettes are placed in a retort in which tissue is processed. In addition, 14 stations supply solutions of various compositions to the retort. User-programmable software controls this automated process. A rotary valve regulates the movement of solutions between the retort and the various stations, applying pressure or vacuums to the retort when the valve is open causes solution to be pumped out of or pumped into the retort, respectively. Upon completion of a processing run, the instrument automatically prompts the user for a cleaning cycle; this requirement can be overridden only if no Paraffin is used.

Typically such conventional methodology demands sending tissue specimens from the operating room, medical office or other sites, to a pathology laboratory sometime during the working day; overnight batch processing of the specimens, so that a tissue specimen suitable for blocking and sectioning is only available on the morning of the next day; and rendering a diagnosis by a pathologist based on microscopic examination of sections prepared from a blocked and sectioned specimen later on that next day. This requires almost 24 hours between receipt of the specimen and delivery of the pathologist's report. Although a shortened version of the conventional method is presently practiced, it is feasible only for small biopsies. These biopsies need to be fixed for at least about 30 minutes before initiating the processing cycle. The instrument processing cycle can be programmed to last a minimum of 70 minutes, but is preferably 2 to 2½ hours. The SAKURA FINETEK microwave system requires samples to be pre-processed in a pre-processing solution (Sakura P/N 7115) for 30 minutes prior to sectioning. Tissue sections must be less than 2.5 mm before microwave processing. The system may take 3-hours or more. Specimens may have to be reprocessed due to sample burning, resulting from poor microwave control, accumulation of extracted cellular solute in the reagent, and/or additional problems inherent to microwave processing. Microwave processing reagents are toxic, corrosive, chemically unstable, form reactive azeotropes, and are insoluble in Paraffin and thus cross-contamination of microwave reagents.

Boon et al. (Eur. J. Morphol. 33:349-358, 1995) use an isopropanol solution and a Paraffin wax solution in two separate reaction chambers, each subject to vacuum and microwave heating, to process tissue specimens for histology. That system requires that tissue specimens be fixed prior to processing and uses a turntable to distribute microwave energy. In addition, the glass container holding the tissue specimens also adsorbs microwave energy and transfers heat to the solution therein.

Milestone (WO 98/05938) provides another alternative for tissue processing in at least three steps: fixing the tissue specimen, simultaneously dehydrating and clearing with dehydrating agent and an essentially lipophilic agent, and impregnating the tissue specimen. Microwave heating is used in the first two steps and elevated pressure is used during the dehydrating/clearing step. The tissue specimen is dried by heating and reduced pressure, and then it is impregnated under vacuum or, alternatively, by applying a cycle of moderate pressure and moderate vacuum.

Therefore, in summary, with current microwave techniques, samples have to be pre-processed in a pre-processing solution, and cut to 1.5 mm or less in thickness, loaded into a loading station and processed using microwaves through a series of chemical reagents. The process may take 3-hours or more and samples may have to be reprocessed because of sample burring resulting from poor microwave control or the presence of water in the reagent.

Considering that the objective is to remove cellular solutes that interfere with Paraffin preservation, and to have a specimen retain its lifelike characteristics, it is critical to keep in mind that the extraction of cellular solute is a function of the molecular diffusivity, solubility of the solute in the solvent, and the concentration gradient in and outside of the specimen. The following equation can then be used to predict molecular diffusivity at a fixed concentration of solvent:

$$D(\text{solvent} \rightarrow \text{Tissue}) = kT/6\pi\mu r \quad \text{(Equation No. 1)}$$

where:
$\mu$=Viscosity in poses
r=radius of diffusing molecule
k=experimental diffusion constant
T=temperature in degrees K The equation suggests that only small molecules with low viscosity could effectively penetrate tissue, and effectively extract cellular solutes at temperatures less than 100° C. Larger molecules like mineral oils as used in U.S. Pat. Nos. 6,793,890, 6,207,408, and 6586713 do not have the proper effect on extraction of cellular solute. In these patents, mineral oil accumulates on the surface of the specimen, causing poor Paraffin adhesion; Oil also contaminates the Paraffin storage vessel results in poor sectioning over the life of the Paraffin. The Paraffin must be replaced at regular intervals. Ideally, the extraction solvent should have the following characteristics:

1. It should have a high capacity for the species being separated into it, namely, water and water soluble cellular components that interfere with Paraffin impregnation.
2. It should be selective, dissolving one or more of the components being separated to a large extent while not dissolving the other components to any large extent.
3. It should be chemically stable.
4. It should be regenerable, so that extracted species can be separated from it readily and it can be reused again and again.
5. It should be inexpensive to keep cost of maintaining solvent inventory and replacing lost solvent low.
6. It should be nontoxic and noncorrosive.
7. It should have a low viscosity.
8. It should not form so stable an emulsion that the phase cannot be separated adequately.
9. It should allow formation of immiscible liquid phases.

SUMMARY

In a single pressure and temperature controllable reaction container, a rapid and automatic extraction of cellular solutes that interferes with the impregnation of liquid Paraffin into tissue specimens is combined with the impregnation of the evacuated space with Paraffin. In particular, some embodiments of the invention optimize reaction parameters such as: temperature, pressure, solvent flow rate, reaction container space velocity, and solvent properties, so that specimens are fixed, dehydrated, cleared, and impregnated to produce a Paraffinized tissue section in one hour or less.

In some embodiments the solvent is recovered and its volatile components are run through a thermocatalytic oxidizing system that convert them to carbon dioxide and water.

In some embodiments the reliance on a mixture of a ketone and a low molecular weight hydrocarbon is based on the following considerations:

1) The inventor concluded that ketones, existing in the liquid state can be used as a primary extraction solvent based upon the above stated equation. They are soluble in cellular solutes and are present in low concentrations or are absent in biological systems. Acetone is an effective solvent for small specimens, less than 1.5 mm. Being polar, Acetone will partition itself into the aqueous phase. It has problems extracting large molecular weight lipids that have hydrophobic groups. Paraffin cannot be directly blended with Acetone. It is also insoluble in Acetone.

2) When ketones are mixed with low molecular weight hydrocarbons, a suitable extraction solvent is produced. One such mixture is Acetone and Hexane or mixed Hexanes (A/H). The mixture is excellent for extracting water, lipids, and other cellular solutes that will interfere with Paraffin impregnation. The mixture also has some unique properties. The solvent Dimethyl Sulfoxide (DMSO) is insoluble in Hexane, and Paraffin is insoluble in Acetone. However, an Acetone-Hexane mixture will dissolve both DMSO and Paraffin. That type of dissolving compound mixture has both polar and non-polar regions within the mixture. A blend of about 60% per weight Acetone and 40% per weight Hexane forms an azeotropic mixture with a boiling point of 49.8° C. The azeotrope can be easily separated from the cellular solutes and regenerated for additional use. Accordingly, the preferred solvent is an azeotropic, non-aqueous dehydrant, that is a solvent mixture that maintains a low boiling point and a low viscosity when combined with the solutes found in tissues. Preferably, the dissolving compound mixture should exhibit a viscosity of no more than 0.35 centipoise at 60° C.

3) The A/H compound is an ideal solvent for tissue preservation. It can remove all necessary cellular components that interfere with Paraffin impregnation in a short time, 10 to 30 minutes. The A/H solvent will saturate a tissue specimen, replace the extractable cellular solutes, and can be removed under normal operation conditions as taught in the present invention. It provides a vehicle for transporting Paraffin into the specimen resulting is very short impregnation times.

4) The throughput-limiting factor in tissue processing is the rate of Paraffin impregnation. The experimental value for diffusivity of Paraffin into breast tissue is $5.0 \times 10\text{-}6$ cm$^2$/sec, at 60° C. and –27 inches Hg. Thus, for a 1.0 mm specimen the impregnation time is greater than 60 minutes. By using an A/H solvent and adding 6% per weight of Paraffin, the impregnation time for a 5.0 mm specimen is only 30 minutes. The blending of the Paraffin with the solvent reduces the viscosity of the Paraffin and allows for faster penetration.

A zeotropic solvent comprising a mixture of Acetone and Xylene or mixed Xylenes (A/X) may also be advantageously used.

The present embodiments may include a buffer to stabilize the extraction solvent to near neutral conditions. Tris-(hydroxymethyl)aminomethane is an excellent buffer for this application, but any compound capable of buffering the solvent at near neutral pH and which is soluble in the extraction solvent is applicable. Other chemicals may be added to the A/H or A/X solvent to increase solvent viscosity. Examples are alcohols, ketones, aldehydes, solvents, and hydrocarbons, e.g. DMSO and 2-propanol. DMSO is an additional extraction solvent that can added to the A/H or A/X solvent. DMSO assists in the extraction of large ring compounds and free nucleotides, e.g., lithocholic acid, deoxycholic acid, cholesterol, and other compounds that interfere with Paraffin impregnation. Alcohols may be added to slow the extraction process and prevent cellular membranes from rupturing.

The present embodiments do not use microwaves. Specimen processing can be completed in approximately one hour. There is little or no significant pre-processing of specimens prior to solvent extraction. Specimens as large as 5 mm can be readily processed.

In some embodiments homogeneous temperature profiles are seen between specimens and solvent. The solvent extraction process can take place in a single pressurized reactor at pressures of between –29.9 inches Hg to 50 psig, extraction temperatures between 30° C. and 100° C., and typical space velocities between 30 and 150 seconds.

In the disclosed embodiments the presence of water in the solvent does not affect the reactor's temperature profile or the specimen's lifelike characteristics as can happen with microwave processing. Excess water from cellular solute extract and other cellular molecules can be further separated during solvent regeneration.

In some embodiments the process does not use microwaves to heat the specimen and chemical reagents. Therefore, a homogeneous temperature throughout the reaction container can be readily maintained. In some embodiments the reaction takes place in a single reaction container, at elevated pressures up to about 3.3 bars (50 psig), temperatures 30° C. to 100° C., and a space velocity between 30 to 150 seconds. In some embodiments the solvent may include Paraffin. In some embodiments Paraffin need not be separated from the solvent in a separate vessel, and there are no robotic or manual transfers of specimens. In some embodiments the Paraffin concentration in the solvent can to increase over the life of the solvent without affecting the lifelike characteristics of the specimens. In some embodiments the solvent/Paraffin mixture can also be used to lubricate pumps used in the processor. The solvent blend can be chemically stable.

In some embodiments specimens are saturated with this dissolving compound. In some embodiments Paraffin impregnation of the specimens does not require vacuum drying or transfer to another vessel prior to Paraffin impregnation as with microwave processing. Specimen and solvent temperatures are homogenous within the reaction container once equilibrium has been reached. In microwave systems, there are different heat transfer rates; the specimens may contain more water than the reagent or vise versa; and different heating rates are used. Consequently, inconsistent results are obtained. Many of the present embodiments provide consistent, lifelike results, faster, without pre-processing requirement, with less cutting (Often, specimens up to 5 mm thick can be processed), without solvent cross-contamination problems, without having to burr specimens, without water contamination problems, and in a single reaction container without the safety problems associated with microwave systems.

Some embodiments provide a tissue flow processing method which comprises: providing a pressure and temperature controllable reaction container; placing at least one fresh tissue specimen in said container; treating said specimen in said container to remove solutes and replace said solutes with Paraffin, said step of treating consisting essentially of: introducing a temperature and pressure conditioned dissolving compound into said container; allowing time for said compound to penetrate said specimen and to dilute solutes therein; flooding said container with liquid Paraffin; vaporizing said compound and allowing a period for said Paraffin to impregnate said specimens; evacuating said compound and diluted solutes from said container; and, reducing the temperature in said container below the melting point of Paraffin.

In some embodiments, the dissolving compound comprises a zeotropic or an azeotropic dehydrant mixture.

In some embodiments the dissolving compound comprises a solvent taken from a group consisting essentially of ketones, esters, alcohols, aldehydes, cyclic compounds, ethers, cyclic ethers, aromatics, low molecular weight hydrocarbons, and a mixture of low molecular weight hydrocarbons.

In some embodiments the dissolving compound consists of a mixture taken from a group consisting essentially of:

a mixture of about 60% per weight Acetone and about 40% per weight at least one Hexane;

a mixture of about 46% per weight Acetone, about 25% per weight at least one Hexane, about 7% per weight DMSO, about 20% per weight 2-Propanol and about 2% per weight Paraffin;

a mixture of about 62% per weight Acetone, about 16% per weight at least one Hexane, about 4% per weight DMSO, about 12% per weight 2-Propanol and about 6% per weight Paraffin;

a mixture of about 17% per weight Acetone, about 39% per weight at least one Hexane, about 5% per weight DMSO, about 12% per weight 2-Propanol and about 30% per weight Paraffin;

a mixture of about 46% per weight Acetone, about 25% per weight at least one Hexane, about 7% per weight DMSO and about 20% per weight 2-Propanol;

a mixture of about 53% per weight Acetone, about 26% per weight at least one Xylene, about 20% per weight Ethanol, and about 1% per weight DMSO; and, a mixture of about 62% per weight Acetone, about 19% per weight at least one Xylene, and about 19% per weight Ethanol.

In some embodiments the method further comprises regenerating dissolving compound evacuated from said container in a regeneration canister. In some embodiments the regenerating comprises distilling said evacuated compound; and converting vent waste gases into carbon dioxide and water through a thermocatalytic oxidizer. In some embodiments the method further comprises conditioning regenerated dissolving compound for introduction into said reaction container. In some embodiments the conditioning comprises heating said dissolving compound in solvent vessel to a temperature of approximately 60° C.; and establishing a pressure of approximately 0.8 bars (12 psig) in said solvent vessel. In some embodiments the time allowed for the dissolving compound to penetrate the specimens is limited to no more than approximately 30 minutes, and said period is limited to no more than approximately 30 minutes. In some embodiments the specimens may be taken from a group consisting essentially of non-processed and non-burred tissue sections 5 mm thick. In some embodiments the penetration time is limited to no more than approximately 30 minutes, and said period is limited to no more than approximately 50 minutes; and the specimens comprise non-processed and non-burred tissue sections 10 mm thick. In some embodiments the method further comprises admitting a limited amount of Paraffin into the container before introducing said the compound.

In some embodiments there is provided a histoprocess which comprises dissolving and removing cellular solutes in a tissue specimen using a single dissolving compound; and replacing said solutes with Paraffin; said process being performed in a continuous sequence of steps within a single vessel. In some embodiments the dissolving compound comprises a solvent taken from a group consisting essentially of ketones, esters, alcohols, aldehydes, cyclic compounds, ethers, cyclic ethers, aromatics, low molecular weight hydrocarbons, and a mixture of low molecular weight hydrocarbons. In some embodiments the dissolving compound comprises Acetone and Hexane.

In some embodiments there is provided a method for treating histological specimens having a sequence of steps which comprises: saturating said specimen with said dissolving compound; flooding said vessel with liquid Paraffin; and vaporating said dissolving compound and said solutes to allow said Paraffin to infiltrate spaces vacated by said compound and solutes.

In some embodiments the steps further comprise: evacuating said mixture and solutes to a regeneration canister; recuperating said mixture by distillation; and disposing of vent gases by thermocatalytic oxidation. In some embodiments the process further comprises mixing said compound in said vessel prior to said dissolving and removing.

In some embodiments there is provided an apparatus for processing tissue specimens against decomposition, putrefaction and autolysis which comprises: a hermetically sealable reaction container; means for controlling the flow, temperature and pressure inside said container; a source of dissolving compound connectable to said container; a source of melted Paraffin connectable to said container; and means for evacuating gases from said container; wherein said dissolving compound comprises a mixture of a ketone and at least one low molecular weight hydrocarbon.

In some embodiments that dissolving compound consists of a mixture taken from a group consisting essentially of:

a mixture of about 60% per weight Acetone and about 40% per weight at least one Hexane;

a mixture of about 46% per weight Acetone, about 25% per weight at least one Hexane, about 7% per weight DMSO, about 20% per weight 2-Propanol and about 2% per weight Paraffin;

a mixture of about 62% per weight Acetone, about 16% per weight at least one Hexane, about 4% per weight DMSO, about 12% per weight 2-Propanol and about 6% per weight Paraffin;

a mixture of about 17% per weight Acetone, about 39% per weight at least one Hexane, about 5% per weight DMSO, about 12% per weight 2-Propanol and about 30% per weight Paraffin;

a mixture of about 46% per weight Acetone, about 25% per weight at least one Hexane, about 7% per weight DMSO and about 20% per weight 2-Propanol;

a mixture of about 53% per weight Acetone, about 26% per weight at least one Xylene, about 20% per weight Ethanol, and about 1% per weight DMSO; and, a mixture of about 62% per weight Acetone, about 19% per weight at least one Xylene, and about 19% per weight Ethanol.

In some embodiments the apparatus further comprises means for regenerating vaporized dissolving compound evacuated from said container. In some embodiments the means for regenerating comprise: a still for recuperating said evacuated dissolving compound; and a thermocatalytic oxidizer for converting vent waste gases into carbon dioxide and water. In some embodiments the dissolving compound in the apparatus comprises a mixture of approximately 17% to 65% per weight Acetone and 16% to 40% per weight Hexane.

In some embodiments there is provided a combination of a tissue specimen with a preparation for dissolving lipids and other cellular solutes in said specimen taken from a group consisting essentially of:

a mixture of about 60% per weight Acetone and about 40% per weight at least one Hexane;

a mixture of about 46% per weight Acetone, about 25% per weight at least one Hexane, about 7.0% per weight DMSO, about 20% per weight 2-Propanol and about 2.0% per weight Paraffin;

a mixture of about 62% per weight Acetone, about 16% per weight at least one Hexane, about 4% per weight DMSO, about 12% per weight 2-Propanol and about 6% per weight Paraffin;

a mixture of about 17% per weight Acetone, about 39% per weight at least one Hexane, about 5% per weight DMSO, about 12% per weight 2-Propanol and about 30% per weight Paraffin;

a mixture of about 46% per weight Acetone, about 25% per weight at least one Hexane, about 7% per weight DMSO and about 20% per weight 2-Propanol;

a mixture of about 53% per weight Acetone, about 26% per weight at least one Xylene, about 20% per weight Ethanol, and about 1% per weight DMSO; and, a mixture of about 62% per weight Acetone, about 19% per weight at least one Xylene, and about 19% per weight Ethanol.

In some embodiments there is provided a process, for removing cellular solutes from a tissue specimen, which comprises treating said specimen with a dissolving compound having a viscosity of no more than 0.35 centipoises at 60° C. and a boiling point of less than 80° C. at 10 torr. In some embodiments the dissolving compound is regenerated after combination with the solutes.

In some embodiments the dissolving compound is regenerated after combination with the solutes. In some histoprocesses, the dissolving compound comprises a lubricant for process pumps and valves. In some embodiments, the Paraffin present in the solvent provides lubricating properties for process pumps and valves. In some embodiments, the dissolving compound is vaporizable at a pressure of no more than 10 torr and a temperature of no more than about 80° C.

In some embodiments, the process for removing cellular solutes from a tissue specimen comprises treating said specimen with a zeotropic dissolving compound having a viscosity of no more than 1.30 centipoises at 60° C. and a boiling point of less than about 80° C. at a pressure of no more than 10 torr. In some embodiments, the dissolving compound has a refractive index of between about 1.350 and about 1,499 at 20° C.

DESCRIPTION OF THE PREFERRED EMBODIMENT(S)

Figure 1:
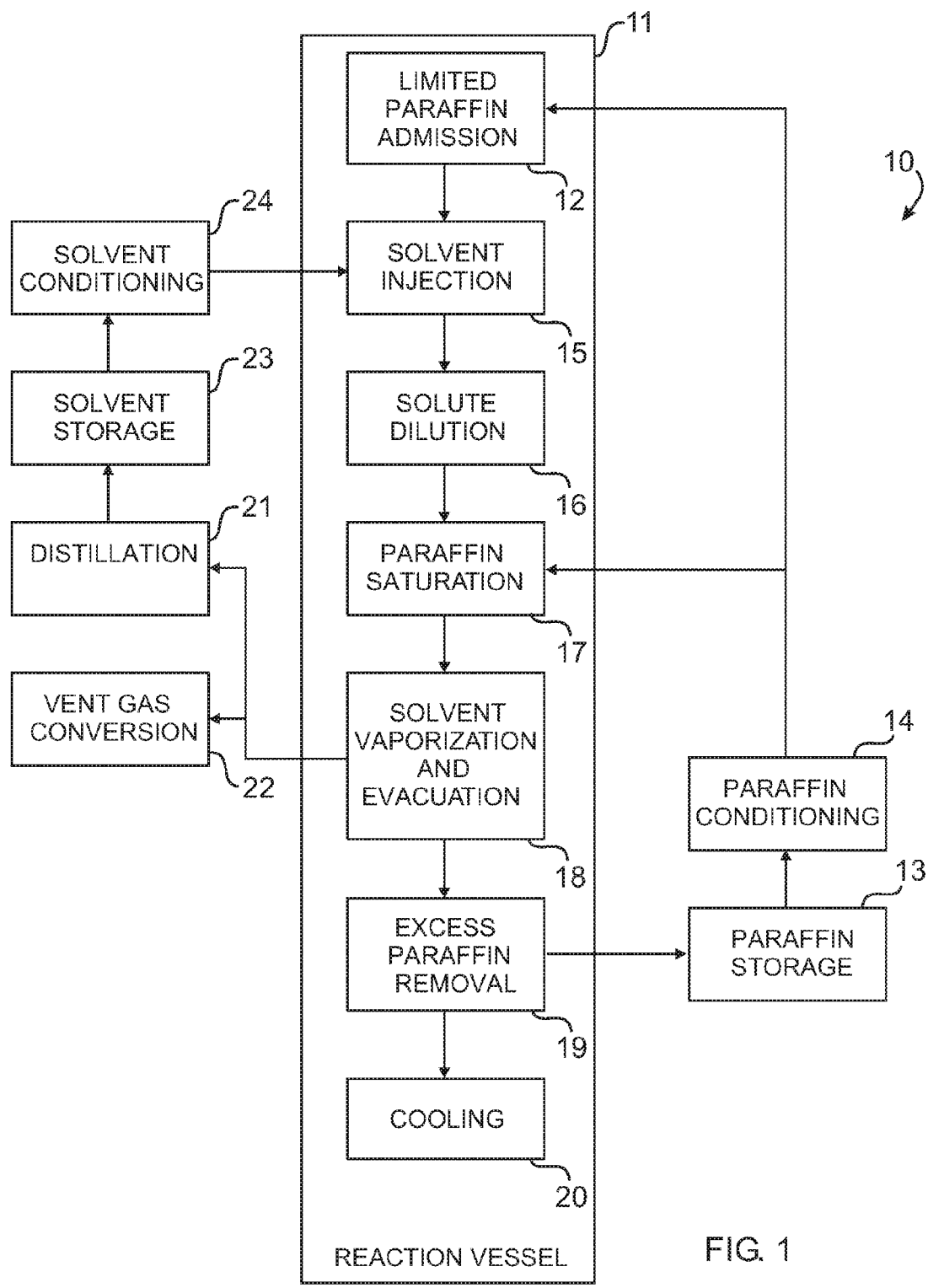
FIG. 1 is a flow diagram of the tissue preserving process according to the invention.
Figure 2:
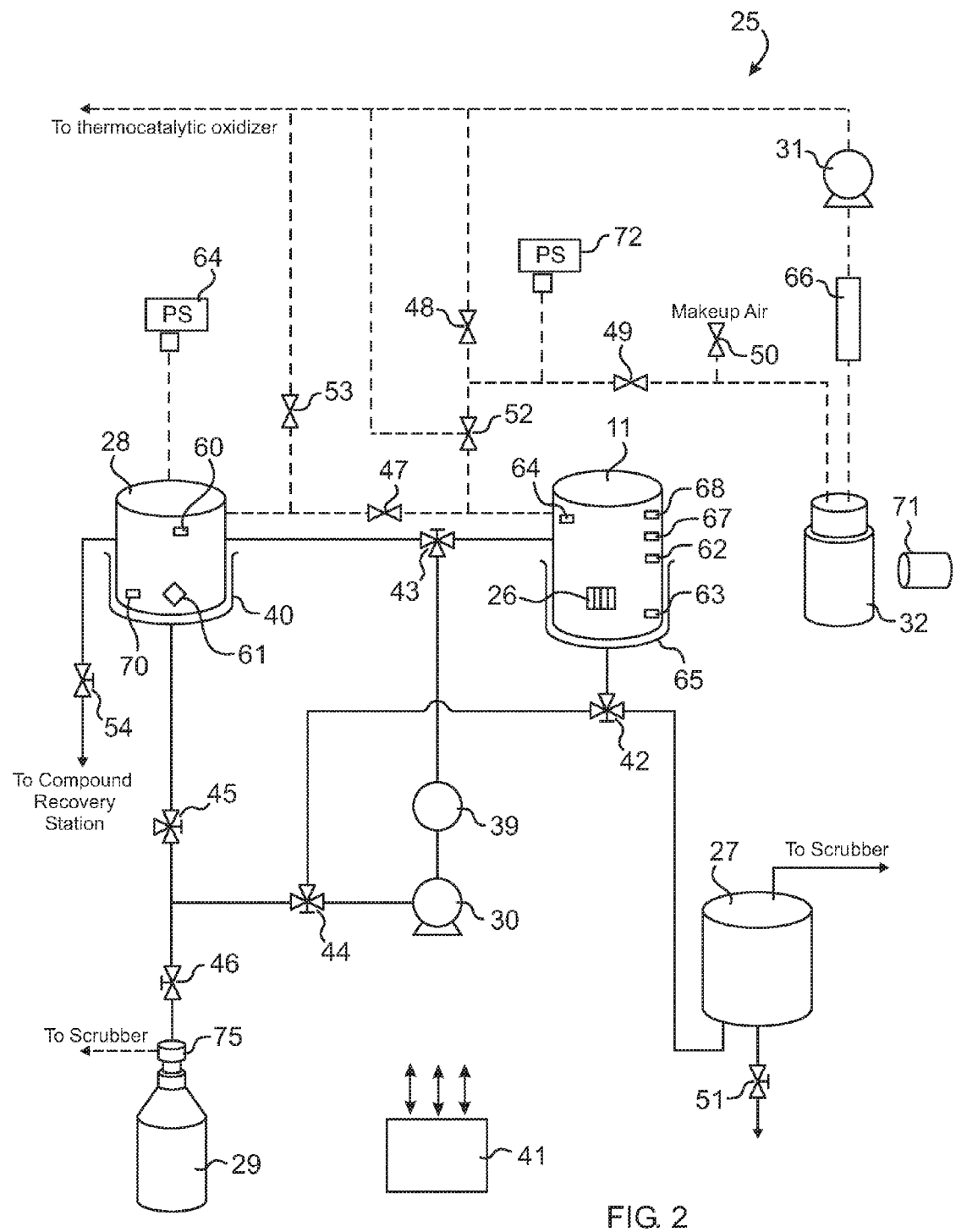
FIG. 2 is a diagrammatical illustration of the apparatus to practice said process.
Figure 3:
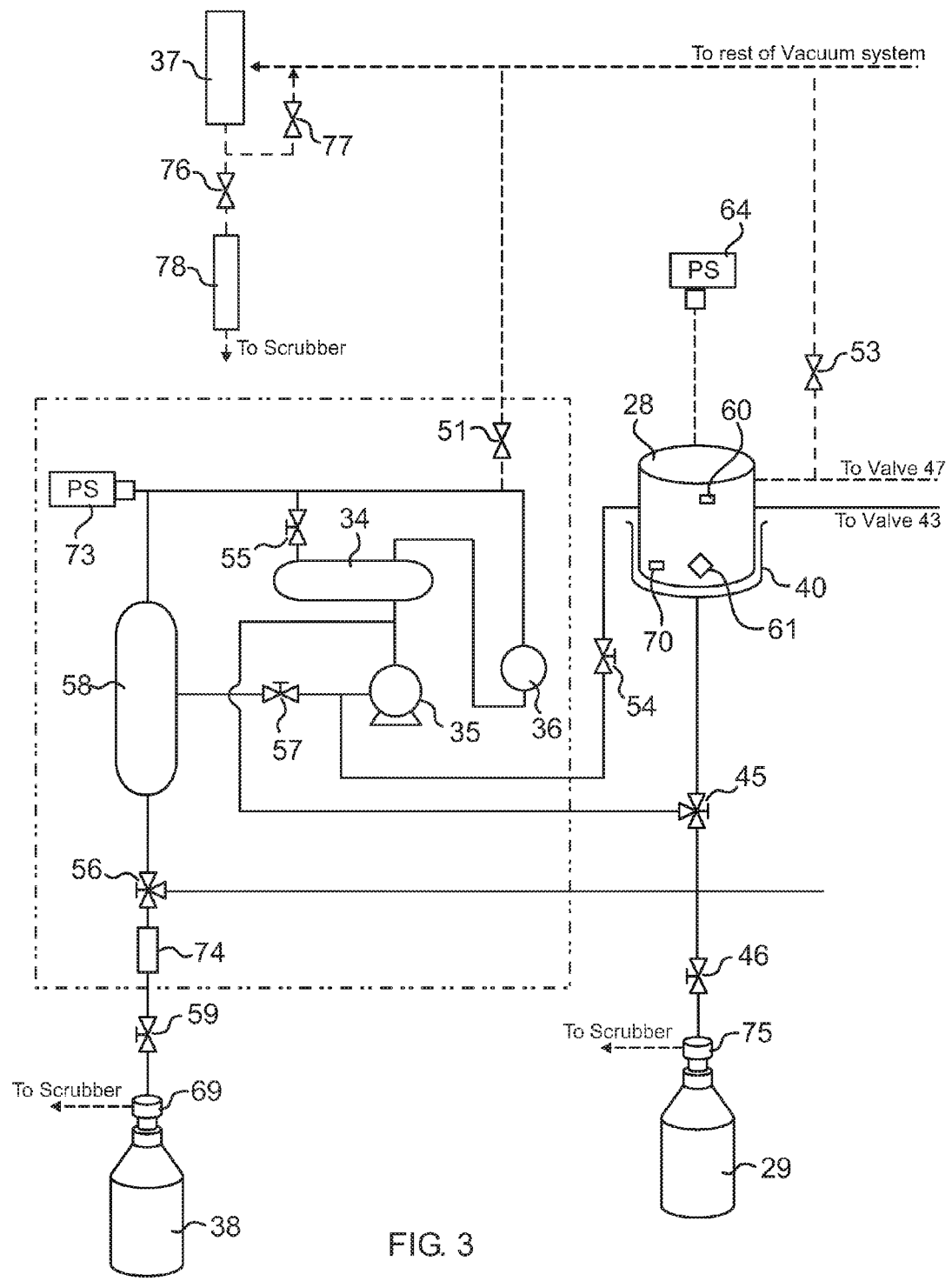
FIG. 3 is a diagrammatical illustration of the solvent regeneration portion of the apparatus.

Referring now to the drawing, there is shown in FIG. 1 the basic steps of a tissue specimen preserving process 10 according to the invention, and, in FIGS. 2 and 3 the instrumentation 25 that may be used to practice the process.

In a hermetically sealable, and pressure and temperature controllable reaction vessel or container 11 in which one or more tissue specimens are being held, a limited volume of melted Paraffin is admitted 12 from a storage tank 13. The Paraffin has been preferably conditioned 14 by raising its temperature slightly above its melting point, e.g., 60° C.

A compound formulated to dissolve cellular solutes in the specimens is injected 15 into the container. These solutes include lipids and other hydrous elements. The compound penetrates the specimens, diluting 16 the solutes. The container is the flooded with Paraffin which saturates 17 the specimens as the dissolving compound is being vaporized and evacuated 18 from the vessel. After removal 19 of excess Paraffin, the reaction vessel is cooled 20 allowing retrieval of the treated specimens.

The evacuated dissolving compound carrying the removed solutes is regenerated by distillation 21 and by converting 22 the waste gases into carbon dioxide and water through a thermocatalytic oxidizer.

The recovered dissolving compound is stored 23 then pressure and temperature preconditioned 24 just prior to being used again in the reaction vessel.

The processing steps and required instrumentation will be now described in greater details.

As illustrated in FIG. 2, the key components of the histoprocessing instrumentation 25 comprise a hermetically sealable, pressure and temperature regulated reaction container 11 sized to hold a number of tissue samples 26. The reaction container is connected by a network of conduits and valves to a source of melted Paraffin constituted by a Paraffin makeup vessel 27, to a source of dissolving compound in the form of a solvent regenerator 28 drawing from a chemical tank 29, to a solvent pump 30, to a vacuum pump 31, and to an overflow reservoir 32. The solvent pump is designed to operate over a wide range of temperatures and pressures.

As shown in FIG. 3, the solvent regenerator 28 is connected to a solvent distillation assembly 33 including an accumulator 34, a recirculation pump 35 and a condenser 36. A thermocatalytic oxidizer 37 is used to breakdown waste gases into water and carbon dioxide. A carbon bed device could be substituted for the oxidizer. The waste material extracted form the used dissolving compound is sent to a waste tank 38. A process heater 39 is provided between the solvent pump and the reaction vessel. A heat exchanger 60 consisting of a 500 watt, explosion-proof bulb is mounted inside the solvent regenerator. A jacket heater 40 surrounds the solvent regenerator. A similar jacket heater 65 surrounds the reaction container. A series of snubber protected pressure sensors 64, 72 and 73 are connected to various areas of the system to regulate pressures.

Valves 41-59, and the pumps 30, 31 and 35 are controlled by a programmable electronic unit 41 according to techniques well known in the industrial process arts.

The process of treating tissue specimen according the invention preferred mode runs as follows.

Tissue specimens are loaded into a stainless steel or polymer constructed basket, and then placed into the reaction container 11. The container cover is then closed and latched. Proximity sensors detect the lid and the process starts. Valve 49 opens and the vacuum pump 31 is started. The pressure of the system is reduced below ambient atmospheric pressure. Valve 49 closes, the vacuum pump is turned off and the system comes to pressure equilibrium. If this condition is not achieved within one minute, a leak is assumed, and the system is shut off.

Preconditioned dissolving compound is transferred from the solvent regenerator 28 to the reaction container 11. Valves 43, 44 and 45 are opened and the reactor jacket heater 65 is energized. The solvent pump 30 and heater 39 are energized. Hot compound fills the reaction container until a solvent level detector switch 67 is triggered. The pressure in the reaction container is regulated by opening valve 47 and the reactor's pressure sensor 64. Valve 45 closes and valve 42 opens. The dissolving compound is recycled and heated in the closed loop consisting of valves 42, 43, and 44, heater 39, solvent pump 30, and the reaction container. At this time, the solvent pump is used to pump up the reactor to an operating pressure as high as about 3.3 bars (50 psig) are used.

Specimens are exposed to the dissolving compound for 10 to 30 minutes. During this exposure, cellular solutes are extracted, (e.g., water, lipids, etc.), and replaced with a mixture of liquid Paraffin and the low molecular hydrocarbons of the compound. Valve 42, 43 and 44, the process heater 39, and the solvent pump 30 are turned off. Hot dissolving compound is transferred from the reaction container to the solvent regenerator. The transfer path includes valves 42, 43, and 44. Valve 47 is opened between the reaction container and the solvent regenerator in order to equilibrate pressure. The transfer lasts until the container's low level indicator switch 63 is reset. At this time, valve 42 is closed and the compound is recycled and reconditioned as later explained.

The reaction container 11 is next flooded with liquid Paraffin as follows. Valve 42 and 49 open, the vacuum pump 31 is turned on. Liquid Paraffin flows into the container until the level indicator switch 67 is triggered. A high level indicator switch 68 in the container acts as a fail-safe device. At this time valve 42 is closed. The saturated specimens are then subjected to a vacuum to extract volatiles.

The pressure in the container is further reduced to evaporate the all dissolving compound present. The diffusion pump 66 is used to reduce pressures to less than 1 torr. Vacuum is applied until pressure equilibrium is achieved, e.g. about 0.9 to 0.99 At. (−27 to −29.91 inches Hg), depending upon solvent. Once equilibrium is reached, all volatile solvent molecules have been removed from the reaction container and specimens. The process is allowed to continue for an additional 10 to 30 minutes depending upon total mass of specimens.

The vacuum system consists of the vacuum pump 31, the diffusion pump 66, and the overflow vessel 32 equipped with a proximity sensor 71, and an isolation valve 49. The overflow vessel acts as an additional fail-safe device in case of failure of the high level indicator switch 68. The air makeup valve 50 is provided to dilute gases prior to entering the thermocatalytic oxidizer 37 and to supply cooling gases to the reaction container during cool down cycles. The pressure sensors 64, 72 and 73 are connected to the control unit 41 in order to monitor all processes of the instrument. Snubbers are employed to prevent liquid from entering the pressure sensors.

In a final step, the Paraffin is returned to the Paraffin makeup vessel 27 as follows. Valves 42, 49 and 50 are opened and the vacuum pump 31 is turned off. Cooling air is drawn through valve 50 and routed to the reaction container. Paraffin is gravitated to the Paraffin makeup vessel 27. During this time, the specimen temperature drops below the Paraffin melt point. The lid of the container opens, the specimen tray is withdrawn and the specimens are extracted and separated.

The following alternate batch solvent blending process may be practiced to prepare a Paraffin-loaded dissolving compound.

Referring to FIG. 2, the reaction container 11 is hermetically sealed. A measured volume of Paraffin-free based solvent is drawn from the chemical tank 29 through a coupler 75 and transferred to the solvent regenerator 28 where it is heated to 60° C. The jacket heater 40 of the solvent regenerator and the vacuum pump 31 are energized. A normally closed control valve 42 is opened and liquid Paraffin is transferred from the Paraffin makeup vessel 27 to the reaction container 11 until a Paraffin level detector 62 inside the reaction container is triggered. At this time, the control valve 42 is closed, and the vacuum pump 31 is stopped. Control valves 43, 44, and 45 are opened and solvent is transferred from the solvent regenerator to the reaction container. When the level detection switch 67 in the reaction container is triggered, the solvent pump 30 is stopped. At this point, all control valves are positioned to create the loop configuration described earlier. The process heater 39 and the solvent pump 30 are energized. The solvent and Paraffin are allowed to blend for about ten minutes into the final dissolving compound. The circuit is reconfigured to transfer the entire blended compound to the solvent regenerator. The reaction container is evacuated. The system is now ready to process specimens. The above described blending sequences of solvent and Paraffin will be omitted in some of the examples described below.

Solvent Regeneration

Recovery and regeneration of the dissolving compound from process streams is desirable, both economically and ecologically. The objective is to recover, purify, and re-use extraction solvents by isolating and filtering cellular solutes from the dissolving compound for waste disposal.

The dissolving compound recovery and regeneration system illustrated in FIG. 3 runs seamlessly with the histoprocess, and does not require frequent attention. For illustration purposes, the following process is described in connection with the Acetone-Hexane (A/H) compound. The recovery and regeneration system is designed to work with many different solvent blends, including both azeotropic and zeotropic blends.

Hot dissolving compound loaded with the removed cellular solutes evacuated from the reaction container 11 is returned to the solvent regenerator 28. A Wheatstone bridge type of conductivity detector 61 associated with the solvent regenerator senses the presence of excess water and cellular solutes, and compares this measurement with the reference conductivity for the pure dissolving compound. When there is a noticeable difference between the measurement and a reference value, hot compound is routed to the packed column 58.

The regeneration process goes as follows. A signal is sent from the conductivity detector 61 to the control unit 41 to initiate the process. Valves 45, 47,49 and 57 open, the recirculation pump 35 is energized and the compound is transferred to the column 58. The process continues until a very low level indicator switch 70 in the solvent regenerator is opened. At this point, the recirculation pump is turned off, and all valves are closed. The entire dissolving compound has now been transferred from the solvent regenerator to the column. If vacuum distillation is required, valves 47, 49, 51, 54, and 55 open. The vacuum pump 31 is energized and the system is pumped down to the required vacuum. Heaters inside the column are activated and the internal temperature is stabilized to 60° C. The condenser 36 and the recirculation pump 35 are energized and the compound is distilled, super-cooled, and collected in the accumulator 34. Valve 57 is partially opened to recycle the product. When the compound reaches a level indicator in the accumulator, valve 54 opens and solvent is transferred to the cooled solvent regenerator 28. The column is optimized by pressure control using valve 55. The control valve 55 provides a bypass from the vapor line to the accumulator. When valve 55 is opened, it equalizes the pressure between the vapor line and the accumulator 34. This causes the condenser 36 to become flooded with condensate. The flooding of the condenser causes the pressure to build up because of the decrease in the active heat transfer surface available decreasing the overhead flow from the column 58 and improving the internal reflux of the column. Under normal operating conditions, super-cooling the condensate causes fluid flow from the condenser 36 to the accumulator 34 and this flow is sufficient to reduce the vapor pressure in the accumulator 34, and allow the column 58 to come to equilibrium for optimized distillation. When the condensing pressure is to be reduced, valve 55 closes, resulting in an increase in the exposed condenser surface area. In order to expose more area, the condensate is transferred to the accumulator. This transfer can occur only if the accumulator vapor pressure has been sufficiently lowered by condensation. Therefore, the system speed in this direction is a function of condensate super-cooling. Increased super-cooling increases system response speed.

The process continues until there is no more liquid buildup in the accumulator. At this point, there is a change in the system pressure sensed by the pressure sensor 73, valve 57 closes and all remaining liquid in the accumulator is transferred to the solvent regenerator. The recirculation pump 35 turns off, all valves close and the heater in the column is turned off. A sensor in the column measures the bottom temperature and when that temperature reaches 60° C., valve 56 opens and the column bottom waste flows into the solvent waste trap 74. A liquid indicator switch is positioned on this trap and opens and closes valve 59. The column waste flows into the waste collection vessel 38 though a bottle coupler 69. When the liquid indicator senses that no fluid remains in the waste trap, valve 59 closes.

Waste Gas Treatment

Vent waste gas (i.e., dissolving compound waste gas) can be disposed of by two methods. The first approach is carbon adsorption currently used in most histoprocessing. Once the carbon is saturated with solvent, it must be treated prior to disposal. A preferable alternative in the present invention users thermocatalytic oxidation. When properly controlled, that process results in a 99.999% conversion of the gas to carbon dioxide and water.

The thermocatalytic oxidizer assembly includes the following elements: a thermocatalytic oxidizer 37, flue gas control valve 76, a recycling path through valve 77, and a flue gas after-cooler 78. A typical thermocatalytic oxidizer comprises two distinct sections, namely, a preheating chamber to elevate the gases to proper reaction temperature, and a catalytic oxidation section to oxidize gases into carbon dioxide and water.

Vent and relief valve gases are routed through the vacuum system to the thermocatalytic oxidizer, either by direct or by venturi connections. Inline thermal conductivity detectors monitor correct vent gas concentration and trigger dilution of these gases with air through valve 50, to obtain the correct reaction mixture. The mixture is then preheated about 500° F. to initiate the reaction. Gases then pass through a heated catalyst bed, where they react to form water vapor, carbon dioxide, and inert gases. Temperature indicators are used to stabilize the reaction temperature. Flue gas detectors are used to analyze the gas for complete oxidation, and, through the control unit, determine the correct amount of recycle gas, and the proper degree of aperture for the flue gas control valve in order to optimize the reaction.

Temperature and Pressure Preconditioning of the Dissolving Compound

The cellular solute extracting mixture is loaded into the chemical tank 29. A bottle coupler 75 provides a connection for solvent transfer and venting. Valves 46, 44 and 43, are open and the solvent pump 30 transfers mixture into the solvent regenerator 28. Valves 47 and 49 are opened to provide a path to the thermocatalytic oxidizer 37. Once the mixture is transferred from the chemical tank to the solvent regenerator, valves 46 and 47 close. The transfer is monitored by level control switches. Valve 45 is opened and the mixture is heated in the regenerator loop, using the process heater 39 and the regenerator jacket heater 40.

Vent gases are delivered to the thermocatalytic oxidizer 37 for oxidation to carbon dioxide and water as follows. Valve 50 is opened, the vacuum pump 31 is energized. Waste gases are delivered to the oxidizer. Once the inline thermal conductivity detector detects room conditions, valve 49 and 50 close and the vacuum pump is turned off. The mixture is heated to the desired temperature and pressure, e.g. 60° C. and about 0.8 bars (12 psig). It should be noted that the solvent regenerator operating conditions are flexible, and that it can heated from 20 to 100° C. and pressurized to from 1 to about 3.5 At. In addition, the variable flow and pressure solvent pump will operate equally over a wide range of temperatures and pressures. A flow orifice may be placed on the discharge to insure proper pump lubrication. Also, it is worth noting that the Paraffin present in the solvent also provides lubricating properties for pumps and valves.

Example 1

TABLE 1.0

Composition of the dissolving compound

| Component | Weight-percent |
|---|---|
| Acetone | 45.8 |
| Hexane | 25.4 |
| DMSO | 7.0 |
| 2-propanol | 19.8 |
| Paraffin | 2.0 |

TABLE 1.1

Typical processing times and specimen type.

| Reference No. | Color code Code | Processing Time (minutes) | Impregnation Time (min) | Tissue Type |
|---|---|---|---|---|
| 101 | green | 10 | 30 | Breast tissue 2 mm |
| 102 | purple | 10 | 30 | liver 2 mm |
| 103 | green | 10 | 30 | liver 2 mm |
| 104 | green | 20 | 30 | liver 5 mm |
| 105 | purple | 30 | 30 | Breast tissue 5 mm |
| 106 | purple | 30 | 30 | Breast tissue 5 mm |
| 107 | green | 20 | 30 | liver 5 mm |
| 108 | purple | 30 | 30 | Breast tissue 4 mm |
| 109 | green | 30 | 30 | liver 4 mm |
| 110 | purple | 30 | 30 | Liver 4 mm |
| 111 | purple | 30 | 30 | Breast tissue 2 mm |
| 112 | purple | 30 | 30 | Breast tissue 4 mm |

Control Samples:

Tissue specimens 2 mm to 5 mm thick were used. The reagents and time schedule provided below is used as the control procedure in all examples. After processing, embedding, and sectioning; reference slides are compared with slides processed by the present exemplary embodiment of the invention. Hematoxylin-eosin staining is used for pathological comparison.

TABLE 1.2

Control Specimen processing Schedule

| Station | Reagent | Time exposure |
|---|---|---|
| 1 | 10% Buffered neutral formalin | 120 min |
| 2 | 10% Buffered neutral formalin | 120 min |
| 3 | 70% Isopropyl alcohol | 30 min. |
| 4 | 80% Isopropyl alcohol | 30 min. |
| 5 | 95% Isopropyl alcohol | 30 min. |
| 6 | 95% Isopropyl | 30 min. |
| 7 | 100% isopropyl alcohol | 45 min. |
| 8 | 100% Isopropyl | 45 min. |
| 9 | Xylene | 45 min. |
| 10 | Xylene | 45 min. |
| 11 | Paraffin | 60 min. |
| 12 | Paraffin | 60 min |
|  | Embed and section |  |

The dissolving compound of Table 1.0 is transferred from the chemical tank to the solvent regenerator and heated for 15 minutes to an equilibrium temperature of 60° C. with a resulting pressure of 0.8 bars (12 psig). The heated compound is then transferred to the reactor container holding specimens listed in Table 1.1.

The container conditions are next equilibrated to 60° C., 0.8 bars (12 psig), a flow rate of 2.35 liter/min, and a space velocity of 91.2-sec. Specimens are processed for individual times as indicated in Table 1.1. After this processing, specimens are super-saturated with the compound. The excess compound is then returned to the regenerator for additional processing, regeneration and solute separation.

Paraffin is next charged into the reaction container. The temperature inside the container is stabilized to 60° C., and a chemical-potential difference is created between the Paraffin and compound-saturated specimens. Vacuum is then used to increase this differential, vaporizing the compound within the specimen, and substituting compound molecules with hot Paraffin. Vacuum is continually applied until a pressure equilibration is achieved. Ten minutes after equilibrium is obtained, the heaters are disengaged, the vent solenoid opens, and the reaction container is brought to room temperature before extracting the specimens.

Results:

Sections of the tissue obtained from the above processing were excellent and virtually indistinguishable from the reference specimens using a light microscope. Breast tissue processed using the present invention did not have to be defatted prior to processing. The solvent removed all lipids that interfere with Paraffin impregnation.

Example 2

The following is an example of batch solvent blending within the reaction container. Table 2.0 shows wt-% of components before and after batch reactor blending.

TABLE 2.0

Solvent Batch blending Composition of Dissolving Compound before and after.

| Component | Wt-% Before Reactor Blending | Wt-% After Reactor Blending |
|---|---|---|
| Acetone | 65.55 | 61.51 |
| Hexane | 16.76 | 15.73 |
| DMSO | 4.59 | 4.31 |
| 2-propanol | 13.11 | 12.30 |
| Paraffin | — | 6.15 |

A measured volume of non-Paraffin based solvent is loaded into the solvent regenerator and heated to 60° C. Liquid Paraffin is transferred into the sealed and heated reaction container until the Paraffin level indicator switch is triggered. Dissolving compound is transferred from the solvent regenerator to the reaction container. The compound and Paraffin are thoroughly blended for 5 minutes. The blend is then transferred to the regenerator. The container is evacuated and loaded with the specimens. The histoprocessing begins.

TABLE 2.1

Typical processing times and specimen type.

| Reference No. | Color code Code | Processing Time (minutes) | Impregnation Time (min) | Tissue Type |
|---|---|---|---|---|
| 201 | green | 10 | 30 | Breast tissue 2 mm |
| 202 | purple | 10 | 30 | liver 2 mm |
| 203 | green | 10 | 30 | liver 2 mm |
| 204 | green | 20 | 30 | liver 5 mm |
| 205 | purple | 30 | 30 | Breast tissue 5 mm |
| 206 | purple | 30 | 30 | Breast tissue 5 mm |
| 207 | green | 20 | 30 | liver 5 mm |
| 208 | purple | 30 | 30 | Breast tissue 4 mm |
| 209 | green | 30 | 30 | liver 4 mm |
| 210 | purple | 30 | 30 | Liver 4 mm |
| 211 | purple | 30 | 30 | Breast tissue 2 mm |
| 212 | purple | 30 | 30 | Breast tissue 4 mm |

The dissolving compound of Table 2.0, in the solvent regenerator, is heated to an equilibrium temperature of 60° C. and a pressure of about 0.8 bars (12 psig), then transferred to the reaction container holding the specimens listed in Table 2.1.

The container conditions are next equilibrated to 60° C., and about 1.6 bars (25 psig), a flow rate of 2.35 liter/min, and a space velocity of 91.2-sec. Specimens are processed for individual times as indicated in Table 2.1. After this processing, specimens are super-saturated with the dissolving compound. The excess compound is then returned to the regenerator for additional processing, regeneration and solute separation.

Paraffin is next charged to the reaction container. The container is stabilized to 60° C., and a chemical-potential difference is created between the Paraffin and compound saturated specimens. Vacuum is then used to increase this differential, vaporizing the compound with in the specimen, and substituting compound molecules with hot Paraffin. Vacuum is continually applied until a pressure equilibration is achieved. Ten minutes after equilibrium is obtained, the heaters are disengaged, the vent solenoid opens, and the reaction container is brought to room temperature before extracting the specimens.

Results:

The section of the tissue obtained from the above processing was excellent and virtually indistinguishable under a light microscope from sample process using the control procedure.

Example 3

The following is another example of batch solvent blending within the reaction container. Table 3.0 shows wt-% of components before and after batch reactor blending.

TABLE 3.0

Solvent Batch blending Composition of Dissolving Compound before and after.

| Component | Wt-% Before Reactor Blending | Wt-% After Reactor Blending |
|---|---|---|
| Acetone | 17.45 | 16.68 |
| Hexane | 43.16 | 38.80 |
| DMSO | 5.63 | 5.06 |
| 2-propanol | 33.76 | 10.12 |
| Paraffin | — | 30.35 |

TABLE 3.1

Typical processing times and specimen type.

| Reference No. | Color code Code | Processing Time (minutes) | Impregnation Time (min) | Tissue Type |
|---|---|---|---|---|
| 301 | green | 10 | 30 | Breast tissue 2 mm |
| 302 | purple | 10 | 30 | liver 2 mm |
| 303 | green | 10 | 30 | liver 2 mm |
| 304 | green | 20 | 30 | liver 5 mm |
| 305 | purple | 30 | 30 | Breast tissue 5 mm |
| 306 | purple | 30 | 30 | Breast tissue 5 mm |
| 307 | green | 20 | 30 | liver 5 mm |
| 308 | purple | 30 | 30 | Breast tissue 4 mm |
| 309 | green | 30 | 30 | liver 10 mm |
| 310 | purple | 30 | 30 | Liver 10 mm |
| 311 | purple | 30 | 30 | Breast tissue 2 mm |
| 312 | purple | 30 | 30 | Breast tissue 4 mm |

The dissolving compound of Table 3.0 in the solvent regenerator is heated to an equilibrium temperature of 60° C. and a pressure of about 0.8 bars (12 psig). The heated compound is then transferred to the reaction container holding the specimens listed in Table 3.1.

The container conditions are next equilibrated to 60° C., about 2.4 bars (36.5 psig0, a flow rate of 2.35 liter/min, and a space velocity of 91.2-sec. Specimens are processed for individual times as indicated in Table 3.1. After this processing, specimens are super-saturated with the dissolving compound. The excess compound is then returned to the regenerator.

Additional Paraffin is next charged to the container. The container is stabilized to 60° C., and a chemical-potential difference is created between the Paraffin and compound-saturated specimens. Vacuum is then used to increase this differential, vaporizing the dissolving compound with in the specimen, and substituting the compound molecules with hot Paraffin. Vacuum is continually applied until a pressure equilibration is achieved. Ten minutes after equilibrium is obtained, the heaters are disengaged, the vent solenoid opens, and the reaction container is brought to room temperature before extracting the specimens.

Results:

The section of the tissue obtained from the above processing was excellent and virtually indistinguishable under a light microscope from sample process using the control procedure.

Example 4

In this example, no Paraffin is added to the solvent mixture. The impregnation set takes an additional 20 minutes.

TABLE 4.0

Composition of Dissolving Compound

| Component | Weight-percent |
|---|---|
| Acetone | 45.8 |
| Hexane | 25.4 |
| DMSO | 7.0 |
| 2-propanol | 19.8 |

TABLE 4.1

Typical processing times and specimen type.

| Reference No. | Color code Code | Processing Time (minutes) | Impregnation Time (min) | Tissue Type |
|---|---|---|---|---|
| 401 | green | 10 | 50 | Breast tissue 2 mm |
| 402 | purple | 10 | 50 | liver 2 mm |
| 403 | green | 10 | 50 | liver 2 mm |
| 404 | green | 20 | 50 | liver 5 mm |
| 405 | purple | 30 | 50 | Breast tissue 5 mm |
| 406 | purple | 30 | 50 | Breast tissue 5 mm |
| 407 | green | 20 | 50 | liver 5 mm |
| 408 | purple | 30 | 50 | Breast tissue 4 mm |
| 409 | green | 30 | 50 | liver 10 mm |
| 410 | purple | 30 | 50 | Liver 10 mm |
| 411 | purple | 30 | 50 | Breast tissue 2 mm |
| 412 | purple | 30 | 50 | Breast tissue 4 mm |

The dissolving compound of Table 4.0 is loaded into the solvent regenerator and heated for 15 minutes to an equilibrium temperature of 60° C. and a resulting pressure of about 0.8 bars (12 psig). The heated compound is then transferred to the reaction container holding samples listed in Table 4.1.

The container conditions are next equilibrated to 60° C., 0.8 bars (12 psig), a flow rate of 2.35 liter/min, and a space velocity of 91.2-sec. Specimens are processed for individual times as indicated in Table 4.1. After this processing, specimens are super-saturated with the dissolving compound. The excess compound is then returned to the regenerator.

Paraffin is next charged to the reaction container. The container is stabilized to 60° C., and a chemical-potential difference is created between the Paraffin and compound saturated specimens. Vacuum is then used to increase this differential, vaporizing the compound with in the specimen, and substituting compound molecules with hot Paraffin. Vacuum is continually applied until a pressure equilibration is achieved. Ten minutes after equilibrium is obtained, the heaters are disengaged, the vent solenoid opens, and the reaction container is brought to room temperature before extracting the specimens.

Results:

The section of the tissue obtained from the above processing was excellent and virtually indistinguishable under a light microscope from sample process using the control procedure.

Example 5

In this example, no Paraffin is directly added to the solvent mixture. Paraffin is used to displace the dissolving compound that has saturated the specimens. The impregnation set takes an additional 20 minutes.

TABLE 5.0

Composition of Dissolving Compound

| Component | Weight-percent |
|---|---|
| Acetone | 59 |
| Hexane | 41 |
| DMSO | |
| 2-propanol | |

TABLE 5.1

Typical processing times and specimen type.

| Reference No. | Color code Code | Processing Time (minutes) | Impregnation Time (min) | Tissue Type |
|---|---|---|---|---|
| 501 | green | 10 | 50 | Breast tissue 2 mm |
| 502 | purple | 10 | 50 | liver 2 mm |
| 503 | green | 10 | 50 | liver 2 mm |
| 504 | green | 20 | 50 | liver 5 mm |
| 505 | purple | 30 | 50 | Breast tissue 5 mm |
| 506 | purple | 30 | 50 | Breast tissue 5 mm |
| 507 | green | 20 | 50 | liver 5 mm |
| 508 | purple | 30 | 50 | Breast tissue 4 mm |
| 509 | green | 30 | 50 | liver 10 mm |
| 510 | purple | 30 | 50 | Liver 10 mm |
| 511 | purple | 30 | 50 | Breast tissue 2 mm |
| 512 | purple | 30 | 50 | Breast tissue 4 mm |

The dissolving compound of Table 5.0 is loaded into the solvent regenerator and heated for 15 minutes to an equilibrium temperature of 60° C. and a resulting pressure of about 0.8 bars (12 psig). The heated compound is then transferred to the reaction container holding the specimens listed in Table 5.1.

The reaction container conditions are next equilibrated to 60° C., about 0.8 bars (12 psig), a flow rate of 2.35 liter/min, and a space velocity of 91.2-sec. Specimens are processed for individual times as indicated in Table 5.1. After this processing, specimens are super-saturated with the compound. The excess compound is then returned to the regenerator.

Paraffin is next charged into the reaction container. The container is stabilized to 60° C., and a chemical-potential difference is created between the Paraffin and compound-saturated specimens. Vacuum is then used to increase this differential, vaporizing the compound within the specimen, and substituting compound molecules with hot Paraffin. Vacuum is continually applied until a pressure equilibration is achieved. Ten minutes after equilibrium is obtained, the heaters are disengaged, the vent solenoid opens, and the reaction container is brought to room temperature before extracting the specimens.

Results:

The section of the tissue obtained from the above processing was excellent and virtually indistinguishable under a light microscope from sample process using the control procedure.

Example 6

The following is an example of batch solvent blending within the reaction container. Table 6.0 shows wt-% of components before and after batch reactor blending.

TABLE 6.0

Solvent Batch blending Composition of Dissolving compound before and after.

| Component | Wt-% Before Reactor Blending | Wt-% After Reactor Blending |
|---|---|---|
| Acetone | 59.0 | 54.0 |
| Hexane | 41.0 | 38.0 |
| Paraffin | — | 8.0 |

TABLE 6.1

Typical processing times and specimen type.

| Reference No. | Color code Code | Processing Time (minutes) | Impregnation Time (min) | Tissue Type |
|---|---|---|---|---|
| 601 | green | 10 | 50 | Breast tissue 2 mm |
| 602 | purple | 10 | 50 | liver 2 mm |
| 603 | green | 10 | 50 | liver 2 mm |
| 604 | green | 20 | 50 | liver 5 mm |
| 605 | purple | 30 | 50 | Breast tissue 5 mm |
| 606 | purple | 30 | 50 | Breast tissue 5 mm |
| 607 | green | 20 | 50 | liver 5 mm |
| 608 | purple | 30 | 50 | Breast tissue 4 mm |
| 609 | green | 30 | 50 | liver 10 mm |
| 610 | purple | 30 | 50 | Liver 10 mm |
| 611 | purple | 30 | 50 | Breast tissue 2 mm |
| 612 | purple | 30 | 50 | Breast tissue 4 m |

The dissolving compound residing in the solvent regenerator is conditioned by heating it to an equilibrium temperature of 60° C. and a pressure of about 0.8 bars (12 psig). The heated compound is then transferred to the reaction container holding the tissue specimens. Any excess compound is returned to the solvent regenerator.

The reaction container conditions are next equilibrated to 60° C., about 1.6 bars (25 psig), a flow rate of 2.35 liter/min, and a space velocity of 91.2-sec. Specimens are processed for individual times as indicated in Table 6.1. After this processing, specimens are super-saturated with the dissolving compound.

Next, the reaction container is flooded with Paraffin. The container is restabilized to 60° C., and a chemical-potential difference is created between the Paraffin and the dissolving compound-saturated specimens. Vacuum is then used to increase this differential, vaporizing the compound within the specimens. The compound molecules are replaced with hot Paraffin. Vacuum is continually applied until a pressure equilibration is achieved. Ten minutes after equilibrium is obtained, the heaters are disengaged, the vent solenoid opens, and the reaction container is brought to room temperature before extracting the specimens.

Results:

The section of the tissue obtained from the above processing was excellent and virtually indistinguishable under a light microscope from sample process using the control procedure.

Example 7

The following is a first example of batch blending ones zeotrope solvent mix, and Paraffin within the reaction container. Table 7.0 shows wt-% of components before and after batch reactor blending.

TABLE 7.0

Zeotrope Solvent blended before and after Paraffin addition.

| Component | Wt-% Before Reactor Blending | Wt-% After Reactor Blending |
|---|---|---|
| Acetone | 53.0 | 50.5 |
| Xylenes | 26.0 | 24.8 |
| Ethanol | 20.0 | 19.0 |
| DMSO | 1.0 | 1.0 |
| Paraffin | — | 4.7 |

Outline of Batch Solvent Blending:

3.8 liters (1 gallon) of non-Paraffin based solvent is placed into the chemical tank 29 and is transferred to the solvent regenerator 28 for heating to 60° C.

The reaction container 11 is sealed, the jacket heater 65 is energized, the vacuum pump 31 is engaged, the control valve 42 is opened and liquid Paraffin is transferred from the Paraffin makeup vessel 27 to the reaction container until the Paraffin level indicator is energized. At this time, the control valve is closed, and the vacuum pump is stopped. Control valves 43, 44, 45 are opened, so that the solvent is transferred from the solvent regenerator to the reaction container. When the high level indicator switch 68 is energized, solvent pump 30 is stopped, and all control valves are positioned to create a reaction container loop configuration. The heat exchanger 60 and solvent pump 30 are energized, and the solvent is blended for ten minutes. The blend loop is reconfigured, so that the blended solvent is then transferred to the solvent regenerator 28. The reaction container is evacuated. The system is now ready to process specimens.

TABLE 7.1

Typical processing times and specimen type.

| Reference No. | Color code Code | Processing Time (minutes) | Impregnation Time (min) | Tissue Type |
|---|---|---|---|---|
| 701 | green | 10 | 30 | Breast tissue 2 mm |
| 702 | purple | 10 | 30 | liver 2 mm |
| 703 | green | 10 | 30 | liver 2 mm |
| 704 | green | 20 | 30 | liver 5 mm |
| 705 | purple | 30 | 30 | Breast tissue 5 mm |
| 706 | purple | 30 | 30 | Breast tissue 5 mm |
| 707 | green | 20 | 30 | liver 5 mm |
| 708 | purple | 30 | 30 | Breast tissue 4 mm |
| 709 | green | 30 | 30 | liver 10 mm |
| 710 | purple | 30 | 30 | Liver 10 mm |
| 711 | purple | 30 | 30 | Breast tissue 2 mm |
| 712 | purple | 30 | 30 | Breast tissue 4 mm |

Tissue Processing:

Extraction solvent (Solvent) in Table 7.0, in the solvent regenerator, is heated to an equilibrium temperature of 60° C. and a pressure of 0.8 bars (12 psig). The heated solvent is then transferred to the reaction container containing samples listed in Table 7.1.

The reaction container conditions are next equilibrated to 60° C., 1.6 bars (25 psig), a flow rate of 2.35 liters/min, and a space velocity of 91.2-sec. Specimens are processed for individual times as indicated in Table 7.1. After this processing, the specimens are super-saturated with the solvent. The excess reaction container solvent is then returned to the solvent regenerator for additional processing, solvent regeneration and solute separation.

Paraffin is next charged to the reaction container via Paraffin makeup vessel. The reaction container is stabilized to 60° C., and a chemical-potential difference is created between the Paraffin and the solvent-saturated specimens. Vacuum is then used to increase this differential, vaporizing the solvent within the specimen, and substituting solvent molecules with hot Paraffin. Vacuum is continually applied until a pressure equilibration is achieved. Ten minutes after equilibrium is obtained, the heaters are disengaged, the vent solenoid opens, and the reaction container is brought to room temperature before extracting the specimens.

Results:

The section of the tissue obtained from the above processing was excellent and virtually indistinguishable under a light microscope from sample process using the control procedure.

Example 8

The following is an example of batch blending of a zeotropic solvent and Paraffin within the reaction container. Table 8.0 shows wt-% of components before and after batch reactor blending.

TABLE 8.0

Zeotrope Solvent blended before and after Paraffin addition.

| Component | Wt-% Before Reactor Blending | Wt-% After Reactor Blending |
|---|---|---|
| Acetone | 62.0 | 58.5 |
| Xylenes | 19.0 | 18.0 |
| Ethanol | 19.0 | 17.9 |
| Paraffin | — | 5.6 |

Outline of Batch Solvent Blending:

3.8 liters (1 gallon) of non-Paraffin based solvent is placed into the chemical tank and is transferred to the Solvent regenerator for heating to 60° C.

The reaction container is sealed, the jacket heater is energized, the vacuum pump is engaged, the control valve 42 is opened and liquid Paraffin is transferred from the Paraffin makeup vessel to the reaction container until the Paraffin level switch is energized. At this time, the control valve is closed, and the vacuum pump is stopped. Control valves 43,44,45 are opened, so that the solvent is transferred from the solvent regenerator to the reaction container. When the high level indicator switch is energized, the solvent pump is stopped, and all control valves are positioned to create a reaction container loop configuration. The heat exchanger and solvent pump are energized, and the solvent is blended for ten minutes. The blend loop is reconfigured, so that the blended solvent is then transferred to the solvent regenerator. The reaction container is evacuated. The system is now ready to process specimens.

TABLE 8.1

Typical processing times and specimen type.

| Reference No. | Color code Code | Processing Time (minutes) | Impregnation Time (min) | Tissue Type |
|---|---|---|---|---|
| 801 | green | 10 | 30 | Breast tissue 2 mm |
| 802 | purple | 10 | 30 | liver 2 mm |
| 803 | green | 10 | 30 | liver 2 mm |
| 804 | green | 20 | 30 | liver 5 mm |
| 805 | purple | 30 | 30 | Breast tissue 5 mm |
| 806 | purple | 30 | 30 | Breast tissue 5 mm |
| 807 | green | 20 | 30 | liver 5 mm |
| 808 | purple | 30 | 30 | Breast tissue 4 mm |
| 809 | green | 30 | 30 | liver 10 mm |
| 810 | purple | 30 | 30 | Liver 10 mm |

TABLE 8.1-continued

Typical processing times and specimen type.

| Reference No. | Color code Code | Processing Time (minutes) | Impregnation Time (min) | Tissue Type |
|---|---|---|---|---|
| 811 | purple | 30 | 30 | Breast tissue 2 mm |
| 812 | purple | 30 | 30 | Breast tissue 4 mm |

Tissue Processing:

Extraction solvent (Solvent) in Table 8.0, in the solvent regenerator, is heated to an equilibrium temperature of 60° C. and a pressure of 0.8 bars (12 psig). The heated solvent is then transferred to the reaction container containing samples listed in table 8.1.

The reaction container conditions are next equilibrated to 60° C., 1.6 bars (25 psig), a flow rate of 2.35 liters/min, and a space velocity of 91.2-sec. Specimens are processed for individual times as indicated in Table 8.1. After this processing, the specimens are super-saturated with the solvent. The excess reaction container solvent is then returned to the solvent regenerator for additional processing, solvent regeneration and solute separation.

Paraffin is next charged to the reaction container via Paraffin makeup vessel. The reaction container is stabilized to 60° C., and a chemical-potential difference is created between the Paraffin and solvent-saturated specimens. Vacuum is then used to increase this differential, vaporizing the solvent within the specimen, and substituting solvent molecules with hot Paraffin. Vacuum is continually applied until a pressure equilibration is achieved. Ten minutes after equilibrium is obtained, the heaters are disengaged, the vent solenoid opens, and the reaction container is brought to room temperature before extracting the specimens.

Results:

The section of the tissue obtained from the above processing was excellent and virtually indistinguishable under a light microscope from sample process using the control procedure.

Other tissue types can be processed using the present invention embodiments, such as but not limited to: appendix, bowel, fallopian tub, kidney, liver, lung, parotid, placenta, prostate, thyroid, adenoma, cervix, skin and many others.

While the preferred embodiments of the invention has been described, modifications can be made and other embodiments may be devised without departing from the spirit of the invention and the scope of the appended claims.

What is claimed is:

1. A specimen processing method comprising:
   treating a specimen in a pressure and temperature controllable reaction container to remove solutes from the specimen and replace the solutes with preserving compound, comprising:
   temperature and pressure conditioning a dissolving compound in a solvent vessel;
   transferring the temperature and pressure conditioned dissolving compound from the solvent vessel to the reaction container, the dissolving compound flowing into the reaction container being in a heated and pressurized condition, the dissolving compound penetrating the specimen and diluting solutes therein, wherein pressure regulation is provided between the solvent vessel and the reaction container during the transferring;
   introducing a preserving compound into the reaction container;
   vaporizing the dissolving compound;
   evacuating the dissolving compound and diluted solutes from the reaction container; and
   reducing the temperature in the reaction container below the melting point of the preserving compound.

2. The method of claim 1 wherein the dissolving compound in the reaction container comprises at least one of azeotropic and zeotropic dehydrant mixtures.

3. The method of claim 1 wherein the dissolving compound comprises a solvent including at least one of ketones, esters, alcohols, aldehydes, ethers, aromatics, low molecular weight hydrocarbons, and a mixture of low molecular weight hydrocarbons.

4. The method of claim 1 wherein the dissolving compound in the reaction container comprises an azeotrope.

5. The method of claim 1 performed without microwave heating.

6. The method of claim 1 further comprising regenerating an amount of the dissolving compound evacuated from the container in a regeneration canister.

7. The method of claim 6 wherein the regenerating comprises distilling the evacuated compound, and converting vent waste gases into carbon dioxide and water through a thermocatalytic oxidizer.

8. The method of claim 6 further comprising conditioning regenerated dissolving compound for introduction into the reaction container.

9. The method of claim 8 wherein the conditioning comprises heating the regenerated dissolving compound to a temperature of approximately 60° C., and establishing a pressure of approximately 0.8 bars.

10. The method of claim 1 wherein the dissolving compound penetrates the specimen and dilutes solutes therein for no more than approximately 30 minutes, and the preserving compound impregnates the specimen for no more than approximately 30 minutes.

11. The method of claim 10 wherein the specimen comprises non-processed and non-burred tissue sections up to 5 mm thick.

12. The method of claim 1 wherein the dissolving compound penetrates the specimen and dilutes solutes therein for no more than approximately 50 minutes, and the preserving compound impregnates the specimen for no more than approximately 50 minutes; and the specimen comprises non-processed and non-burred tissue sections up to 10 mm thick.

13. The method of claim 1 further comprising admitting the liquid preserving compound into the container before introducing the dissolving compound.

14. The method of claim 1 wherein the dissolving compound has a refractive index between about 1.350 and 1.499 at 20° C.

15. The method of claim 1 wherein the dissolving compound comprises a lubricant for process pumps and valves.

16. The method of claim 1 wherein the dissolving compound comprises a mixture of approximately 17% to 65% per weight Acetone and 16% to 40% per weight of at least one Hexane.

17. The method of claim 1 wherein the dissolving compound is vaporizable at a temperature in the range of 30 to 100° C.

18. The method of claim 17 wherein the dissolving compound has a refractive index between about 1.350 and 1.499 at 20° C.

19. The method of claim 1 wherein the reaction container is pressurized during diluting of the solutes.

20. The method of claim 1 wherein pressure regulation is provided by a valve located in a fluid line connecting the solvent vessel and the reaction container.

21. The method of claim 1 wherein the solutes comprise lipids.

* * * * *